United States Patent
Kiel et al.

(10) Patent No.: US 7,273,623 B2
(45) Date of Patent: *Sep. 25, 2007

(54) PROCESS FOR PREPARING TANNATE TABLET, CAPSULE OR OTHER SOLID DOSAGE FORMS

(75) Inventors: Jeffrey S. Kiel, Gainesville, GA (US); H. Greg Thomas, Villa Rica, GA (US); Narasimhan Mani, Gainesville, GA (US)

(73) Assignee: Kiel Laboratories, Inc., Gainesville, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/269,027

(22) Filed: Oct. 10, 2002

(65) Prior Publication Data

US 2003/0077321 A1  Apr. 24, 2003

Related U.S. Application Data

(60) Provisional application No. 60/328,990, filed on Oct. 12, 2001.

(51) Int. Cl.
*A61K 9/14* (2006.01)
*A61K 9/20* (2006.01)
*A61K 9/48* (2006.01)

(52) U.S. Cl. ............ 424/489; 424/451; 424/452; 424/464; 424/465

(58) Field of Classification Search ........... 424/451, 424/452, 464, 465, 489
See application file for complete search history.

(56) References Cited

U.S. PATENT DOCUMENTS

| | | | |
|---|---|---|---|
| 2,950,309 A * | 8/1960 | Cavallito | 560/68 |
| 3,197,370 A * | 7/1965 | Hanus et al. | 514/161 |
| 3,282,789 A | 11/1966 | Marty et al. | |
| 3,591,680 A | 7/1971 | Greene et al. | |
| 4,309,989 A | 1/1982 | Fahim | |
| 4,552,899 A | 11/1985 | Sunshine et al. | |
| 4,619,934 A | 10/1986 | Sunshine et al. | |
| 4,749,697 A | 6/1988 | Sunshine et al. | |
| 4,749,711 A | 6/1988 | Sunshine et al. | |
| 4,749,721 A | 6/1988 | Sunshine et al. | |
| 4,749,722 A | 6/1988 | Sunshine et al. | |
| 4,749,723 A | 6/1988 | Sunshine et al. | |
| 4,767,402 A | 8/1988 | Kost et al. | |
| 4,839,354 A | 6/1989 | Sunshine et al. | |
| 5,025,019 A | 6/1991 | Sunshine et al. | |
| 5,164,398 A | 11/1992 | Sims et al. | |
| 5,599,846 A * | 2/1997 | Chopdekar et al. | 514/653 |
| 5,614,178 A | 3/1997 | Bloom et al. | |
| 5,663,415 A | 9/1997 | Chopdekar et al. | |
| 5,759,579 A | 6/1998 | Singh et al. | |
| 6,037,358 A | 3/2000 | Gordziel | |
| 6,063,770 A | 5/2000 | Falcon | |
| 6,117,452 A | 9/2000 | Ahlgren et al. | |
| 6,187,315 B1 | 2/2001 | Falcon | |
| 6,287,597 B1 * | 9/2001 | Gordziel | 424/464 |
| 6,306,904 B1 | 10/2001 | Gordziel | |
| 6,869,618 B2 * | 3/2005 | Kiel et al. | 424/489 |

FOREIGN PATENT DOCUMENTS

GB  894609  4/1962

OTHER PUBLICATIONS

Cypress Pharmaceutical, Inc., "R-Tannic-S A/D," RX Only, Cypress Pharmaceutical, Inc. (Madison, MS), p. 1, 2, (Mar. 1, 2001).
DSC Laboratories, "Phenylephrine Tannate / Pyrilamine Tannate Suspension," RX Only, DSC Laboratories (Muskegon, MI), p. 1, 2, (Aug. 1, 2001).
Ronald Goldberg, M.D., and Franklin Shuman, M.D., "Evaluation of a Prolonged Action Oral Antihistaminic Preparation as Treatment for Allergic Disorders," Clinical Report, Clinical Medicine (Washington), vol. 72 (No. 9), p. 1475-1479, (Sep. 1, 1965).
John Weiler, M.D., et al, "Randomized, double-blind, parallel groups, placebo-controlled study of efficacy and safety of Rynatan in the Treatment of allergic rhinitis using an acute model ," Annals of Allergy, ACAI (Iowa City, IA), vol. 64 (No. 1), p. 63-67, (Jan. 1, 1990).
Heybach J P et al, "Dietary Quinine Reduces Body Weight and Food Intake Independent of Aversive Taste", Physiology & Behaviour, vol. 29, 1982, pp. 1171-1173, abstract only.

* cited by examiner

*Primary Examiner*—S. Tran
(74) *Attorney, Agent, or Firm*—King & Schickli PLLC

(57) ABSTRACT

An active pharmaceutical ingredient is combined with tannic acid to form a tannate salt complex of the active ingredient. The active ingredient tannate salt complex without isolation or purification is then blended with pharmaceutically acceptable excipients to form a granulate which is processed into a tablet or capsule to generate a therapeutic solid dosage form.

17 Claims, No Drawings

PROCESS FOR PREPARING TANNATE TABLET, CAPSULE OR OTHER SOLID DOSAGE FORMS

PRIOR APPLICATION

This application claims priority from provisional application Ser. No. 60/328,990, filed Oct. 12, 2001.

BACKGROUND OF THE INVENTION

1. Field of the Invention

The present invention relates generally to the field of tannate chemistry and more specifically to methods for preparing tannate pharmaceutical solid dosage forms.

2. Description of the Prior Art

The use of tannate salts for pharmaceutical use is well-known for sustained release applications and patient compliance. U.S. Pat. No. 6,287,597 describes tannate products containing pyrilamine tannate and phenylephrine tannate. There, the suspension is prepared in a conventional manner in that pyrilamine tannate and phenylephrine tannate salts are obtained as the active pharmaceutical ingredients (APIs) and are prepared as a suspension formulation by the addition of suitable pharmaceutical excipients. One teaspoon contains 30 mg pyrilamine tannate and 5 mg phenylephrine tannate with benzoic acid, coloring agent, natural and artificial flavors, glycerin, kaolin, magnesium aluminum silicate, methyl paraben, pectin, purified water, saccharin, sodium hydroxide and sucrose or sorbitol. The January 1990 issue of *Annals of Allergy*, Volume 64, describes combinations of chlorpheniramine tannate, pyrilamine tannate and phenylephrine tannate. An article in *Clinical Medicine*, dated September 1965, pages 1475-1478 describes tablets of pyrilamine tannate, chlorpheniramine tannate and amphetamine tannate. Phenylephrine tannate compositions are disclosed in U.S. Pat. No. 5,599,846 and phenylephrine tannate and chlorpheniramine tannate compositions are disclosed in U.S. Pat. No. 6,037,358. None of these references describe the problems with tannate pharmaceutical products caused by the large size of the tannate molecule. Because of its size, the percentage of active free-base within the tannate salt is significantly lower than that in other salt forms such as the hydrochloride or maleate. The presence of low active percentages and the variable purity of the commercially available tannate salts leads to the stoichiometry of the active free-base to tannic acid in the tannate salts to be different from batch to batch. This problem was noted in U.S. Pat. Nos. 5,599,846 and 5,663,415. This causes significant processing problems during manufacture and increases the likelihood that commercially available pharmaceutical products contain variable and in some instances, sub-therapeutic levels of the active drug substances creating dosing problems. Therefore, it would be desirable if solid dosage form pharmaceutical compositions containing tannate salts of active ingredients could be prepared with reduced variability in active drug content and increased certainty that the active drug is delivered within the therapeutic range. Such a solid dosage form is needed to improve patient compliance with dosage requirements.

SUMMARY OF THE INVENTION

The present invention provides a novel manufacturing process for the conversion of one or more active pharmaceutical ingredients ("API") into their tannate salt complexes while incorporating the complexes into a therapeutic solid-dosage form which also may include non-tannate APIs.

The process provides the addition of the active pharmaceutical ingredients to tannic acid in the presence of a pharmaceutically acceptable liquid which generates tannate salt complexes. Without further treatment, the tannate salt complex of one or more APIs may be combined with pharmaceutically acceptable excipients such as diluents, binders, lubricants, glidants, coloring, sweetening and flavoring agent and processed into suitable solid-dosage forms. The tannate salt complexes of the active ingredient are significantly larger and may afford absorption of the active over prolonged intervals of time. In addition, tannate salts have been found to have better organoleptic properties in comparison to other salts or freebase forms.

By forming the tannate salt complex of one or more active pharmaceutical ingredients, the invention also provides an efficient and reproducible method to manufacture solid-dosage forms that solves the problems referenced above in the prior art. The invention also may afford a prolonged release of active pharmaceutical ingredients over longer intervals of time, thereby reducing the frequency of drug administration and improving patient compliance.

DETAILED DESCRIPTION OF THE INVENTION

The present invention provides a novel manufacturing process for the conversion of one or more active pharmaceutical ingredients (API) into their tannate salt complexes while incorporating the complexes into solid dosage forms, which also may include non-tannate APIs. The first step of this process is to create a tannic acid powder blend by combining an API with tannic acid in the presence of a pharmaceutically acceptable liquid. An anti-clumping agent also may be added to the mix. The presence of the anti-clumping agent prevents the aggregation of the tannate salt complex formed and promotes uniformity in the powder blend.

The conversion process requires the presence of basic functional groups such as amines and sulfoxides in the molecular structure of the API. The source of the tannic acid is natural or synthetic. The formation of the tannate salt is by reaction of amine groups (in the 1°, 2°, 3°,4°, or amphoteric functional states) or of the other basic functional groups with tannic acid. The amount and ratio of anti-clumping agent and tannic acid required for the completion of the reaction is determined by the molecular configuration and concentration of the API.

One or more API tannate salt complex obtained from the above-conversion process is mixed with a diluent, binder(s,) lubricants, sweetening, hardness increasing, coloring, flavoring and flow agents as necessary. The resulting granulate is processed into tablet, capsule or other solid-dosage forms as necessary.

By starting with a known amount of commonly available salt or the free base form of the API, which is subsequently converted and incorporated as a tannate salt complex into a solid dosage form, the invention provides an efficient and reproducible method to manufacture products containing tannate salt complexes as active ingredients. Since the tannate salt complex of the API is generated and incorporated into the dosage form during the manufacturing process, the need to isolate the tannate salt is eliminated and the stoichiometry of the tannate salt is uniform from batch to batch.

The following is a non-exclusive list of active pharmaceutical ingredients that may be used in this process:
(1) carbinoxamine
(2) chlorpheniramine
(3) pyrilamine
(4) pheniramine
(5) phenindamine
(6) diphenhydramine
(7) bromodiphenhydramine
(8) triplennamine
(9) brompheniramine
(10) loratadine
(11) desloratidine
(12) fexofenadine
(13) carbetapentane
(14) dextromethorphan
(15) phenylephrine
(16) pseudoephedrine
(17) ephedrine
(18) oxycodone
(19) morphine
(20) physostigmine
(21) cimetidine
(22) amantidine
(23) fluvoxamine
(24) sertraline
(25) chlorpromazine
(26) imipramine
(27) amitryptyline
(28) prochlorperazine
(29) cetirizine
(30) hydroxyzine
(31) promethazine
(32) acrivastine
(33) triprolidine
(34) meclizine
(35) dimenhydrinate
(36) dexchlorpheniramine
(37) doxylamine
(38) diphenylpyrilamine
(39) trimeprazine
(40) chlorcylizine
(41) triphennamine
(42) codeine
(43) cyproheptadine
(44) phenyltoloxamine
(45) clemastine
(46) famotidine
(47) hydrocodone
(48) methscopolamine
(49) ncostigmine
(50) gabapentin
(51) lithium compounds
(52) dopamine
(53) bromocriptine
(54) carbamazepine
(55) desipramine
(56) nortriptyline
(57) quinidine
(58) procainamide
(59) ranitidine
(60) quinine The excipients commonly used in the formulations are as follows: Microcrystalline cellulose (Avicel), lactose, Mannitol and Di-Pac (compressible sugar) as diluents; magnesium aluminum silicate, xanthan gum, polyvinylpyrrolidone and cellulose compounds as anti-clumping agents; starch hydroxypropyl methylcellulose (HPMC E-10) and xanthan gum as binders; sweetening agents such as sucrose, saccharin sodium, Sucralose and Magnasweet; calcium phosphate as hardness enhancer; talc as a glidant and magnesium stearate as a lubricant. Active ingredients not present as tannate salt complexes also can be included in the formulation.

The salts of the active ingredients are preferably dissolved in purified water. However, other pharmaceutically acceptable liquids can be substituted for water such as isopropyl alcohol, ethanol, glycerin, propylene glycol, mineral oil or mixtures thereof. This leads to the dissociation of the salt into its free-base and conjugate acid forms.

The following EXAMPLES illustrate the conversion process and subsequent incorporation of the tannate salt complexes into suitable solid dosage forms.

EXAMPLE 1

Preparation Of A Dosage Form With One API:

| Ingredient | Amount (g) |
| --- | --- |
| diphenhydramine HCl | 12.500 |
| tannic acid | 32.813 |
| purified water | 12.5 mL |

The ingredients used in the conversion process to generate 25 g of diphenhydramine as the tannate salt complex are shown above. Diphenhydramine hydrochloride and tannic acid are placed in a suitable planetary mixer or blender and the powders are mixed for a period of ten minutes to obtain a uniform powder blend of the ingredients. Once the powders are mixed and a uniform blend obtained, the water is sprayed onto the mixing powders and mixing is continued for ten to fifteen minutes to generate the tannate salt complex of diphenhydramine. The synthetic process yields diphenhydramine tannate salt complex as a uniformly distributed powder mass. The weight ratio of diphenhydramine to tannic acid used is 1:3.

The powder mass of the tannate salt complex obtained from the conversion step is used as is for incorporation into capsules or subsequently can be dried and blended with more diluent, hardness increasing and coloring agents as necessary to form a tablet. A typical tablet composition prepared by well known conventional manufacturing techniques is shown below.

| Ingredient | mg/tablet |
| --- | --- |
| diphenhydramine tannate* | 25.000 |
| magnesium aluminum silicate, NF | 6.750 |
| Avicel PH 102 | 157.181 |
| Sodium Saccharin | 4.500 |
| Methocel E-10 M | 6.750 |
| corn starch | 4.500 |
| Di-Pac | 244.175 |
| calcium phosphate dibasic | 13.500 |
| xanthan gum | 7.875 |
| strawberry flavor | 4.500 |
| talc | 2.250 |
| FD&C Blue No. 2 | 0.450 |
| magnesium stearate | 2.250 |

*equivalent to 12.5 mg diphenhydramine HCl

EXAMPLE 2

Preparation of a Tablet Dosage Form with Two APIs:

The conversion process used to synthesize the tannate salt complexes of two APIs can be performed using the following procedure. For each active, carbetapentane citrate and pseudoephedrine hydrochloride, about 50 ml of purified water is placed in a suitable vessel and the active is added to the water and dissolved. Avicel, tannic acid and magnesium aluminum silicate are placed in a suitable planetary mixer or blender and the powders are mixed for a period of ten minutes to obtain a uniform powder blend of the ingredients. Once the powders are mixed and a uniform blend is obtained, a solution of the actives are added on to the mixing powders and mixing is continued for ten to fifteen minutes to generate the tannate salt complex of carbetapentane and pseudoephedrine. Each API solution also can be added to individual powder blends and the two powder blends can be subsequently mixed. The powder mass containing tannate salt complexes of the API is directly wet granulated by the addition of an aqueous solution of binder. The granulation is subsequently dried and dry blended with more diluent, such as Di-Pac, sweetening, hardness increasing and coloring agents as necessary to form a chewable tablet. A typical tablet composition is shown below.

| Ingredient | mg/tablet |
|---|---|
| carbetapentane tannate* | 25.00 |
| pseudoephedrine tannate** | 75.000 |
| magnesium aluminum silicate, NF | 24.750 |
| Avicel PH 102 | 111.810 |
| Sucralose | 7.500 |
| citric acid | 1.500 |
| Sodium Saccharin | 9.000 |
| Methocel E-10 M | 6.00 |
| Di-Pac | 258.000 |
| Magnasweet - MM100 | 21.00 |
| calcium phosphate dibasic | 18.000 |
| xanthan gum | 13.500 |
| talc | 2.100 |
| magnesium stearate | 2.100 |
| artificial cherry flavor | 12.000 |

*equivalent to 20 mg carbetapentane citrate
**equivalent to 75 mg of pseudoephedrine HCL
The ratio of carbetapentane to tannic acid in the tannate salt complex is 1:1 and pseudoephedrine to tannic acid is 1:2, by weight.

EXAMPLE 3

Preparation of a Tablet Dosage Form with Three or More APIs:

The conversion process used to synthesize the tannate salt complex of carbetapentane, phenylephrine and chlorpheniramine are performed with aqueous solutions of carbetapentane citrate, chlorpheniramine maleate and pseudoephedrine hydrochloride, using the procedure as set forth in EXAMPLE 2. Each API solution can be added to the same powder blend or to individual powder blends and can be subsequently mixed. The powder mass containing the tannate salt complexes is directly wet granulated by the addition of a solution of corn starch. The granulation is subsequently dried to remove the water and dry blended with more diluent, hardness increasing and coloring agents as shown to make the tablets. A typical tablet composition is shown below.

| Ingredient | mg/tablet |
|---|---|
| carbetapentane tannate* | 60.000 |
| chlorpheniramine tannate** | 4.000 |
| phenylephrine tannate*** | 10.000 |
| magnesium aluminum silicate, NF | 30.000 |
| Avicel PH 102 | 459.642 |
| Methocel E-10 M | 5.000 |
| corn starch | 3.000 |
| calcium phosphate dibasic | 10.133 |
| xanthan gum | 7.875 |
| talc | 2.250 |
| FD&C Red #40 | 0.850 |
| magnesium stearate | 2.250 |

*equivalent to 30 mg carbetapentane citrate
**equivalent to 2.5 mg chlorpheniramine maleate
***equivalent to 5 mg phenylephrine hydrochloride
The ratios of carbetapentane, chlorpheniramine and phenylephrine to tannic acid, in the tannate salt complexes, is 1:3, by weight.

EXAMPLE 4

Preparation of a Tablet Dosage Containing Tannate and Non-Tannate APIs:

The conversion process used to synthesize the tannate salt complex of pyrilamine is performed with an aqueous solution of pyrilamine maleate using the procedure as outlined in EXAMPLE 2. The tannate salt complex obtained is then directly wet granulated by the addition of suitable polymers and by spraying an aqueous solution of a binder. The granulation can subsequently be dried and mixed with dextromethorphan HBr, more diluent, hardness increasing and coloring agents as necessary. Dextromethorphan HBr can also be mixed with the tannate salt complex at the wet granulation stage, if required. A typical tablet composition prepared by well known conventional manufacturing techniques is shown below.

| Ingredient | mg/tablet |
|---|---|
| pyrilamine tannate* | 30.000 |
| dextromethorphan HBr | 10.000 |
| magnesium aluminum silicate, NF | 20.000 |
| Mannitol | 403.642 |
| Methocel E-10 M | 5.000 |
| corn starch | 3.000 |
| calcium phosphate dibasic | 10.133 |
| xanthan gum | 7.875 |
| talc | 2.250 |
| FD&C Red #40 | 0.850 |
| magnesium stearate | 2.250 |

*equivalent to 16 mg of pyrilamine maleate
The ratio of pyrilamine to tannic acid in the tannate salt complex is 1:1.5, by weight.

EXAMPLE 5

Preparation of a Capsule Dosage Form with One API:

The powder mass of the tannate salt complex from the conversion step can be mixed with a diluent, flow agents and lubricants. The powder mixture subsequently can be filled into size 2 capsules. A typical capsule formulation prepared by well known conventional encapsulation techniques is shown below.

| Ingredient | mg/capsule |
|---|---|
| brompheniramine tannate* | 12.000 |
| magnesium aluminum silicate, NF | 30.000 |
| Avicel PH 102 | 353.500 |
| talc | 2.250 |
| magnesium stearate | 2.250 |

*equivalent to 6 mg brompheniramine maleate
The ratio of brompheniramine to tannic acid in the tannate salt complex is 1:1.7, by weight.

EXAMPLE 6

Preparation of a Capsule Dosage Form with Two APIs:

The powder mass of the tannate salt complexes of the two APIs obtained from the conversion step can be processed in a similar fashion as in EXAMPLE 5. The tannate salt complexes are mixed with a diluent, flow agents and lubricants. The powder mixture can subsequently be filled into size 1 capsules. A typical capsule formulation prepared by well known conventional encapsulation techniques is shown below.

| Ingredient | mg/capsule |
|---|---|
| diphenhydramine tannate* | 25.000 |
| phenylephrine tannate** | 12.500 |
| PVP | 20.000 |
| Mannitol | 528.000 |
| talc | 2.250 |
| magnesium stearate | 2.50 |

*equivalent to 12.5 mg of diphenhydramine HCl
**equivalent to 2.5 mg phenylephrine HCl
The ratio of diphenhydramine to tannic acid in the tannate salt complex is 1:1.3 and phenylephrine to tannic acid is 1:2, by weight.

EXAMPLE 7

Preparation of a Capsule Dosage Form with Three or More APIs:

The conversion process to generate the tannate salt complexes can be performed by using a powder blend to which the solutions of all three APIs are added, or each API solution is individually added to its own blend. The tannate salt complexes are mixed with a diluent, flow agents and lubricants. The powder mixture subsequently can be filled into size 1 capsules. A typical capsule formulation prepared by well known conventional encapsulation techniques is shown below.

| Ingredient | mg/Capsule |
|---|---|
| carbetapentane tannate* | 60.000 |
| chlorpheniramine tannate** | 4.000 |
| diphenhydramine tannate*** | 25.000 |
| magnesium aluminum silicate, NF | 30.000 |
| Avicel PH 102 | 506.500 |
| Di-Pac (compressible sugar) | 70.000 |

-continued

| Ingredient | mg/Capsule |
|---|---|
| talc | 2.250 |
| magnesium stearate | 2.250 |

*equivalent to 40 mg carbetapentane citrate
**equivalent to 2.5 mg chlorpheniramine maleate
***equivalent to 12.5 mg diphenhydramine HCl
The ratio of carbetapentane to tannic acid in the tannate salt complex is 1:1.4, chlorpheniramine to tannic acid is 1:1.3 and diphenhydramine to tannic acid is 1:1, by weight.

The foregoing is considered as illustrative only of the principles of the invention. Various equivalents to the ingredients may be substituted without departing from the scope thereof. Only such limitations shall be placed thereon as are imposed by the prior art and which are set forth in the appended claims.

What is claimed is:

1. A process for the conversion of at least one active pharmaceutical ingredient in salt or free base form into a tannate salt complex for incorporation into a therapeutic tablet, capsule or other solid dosage form, the process comprising, combining the salt or free base of the at least one active pharmaceutical ingredient with an anti-clumping agent and tannic acid in the presence of a pharmaceutically acceptable liquid to form a tannate salt complex of at least one active pharmaceutical ingredient, tannic acid and anti-clumping agent for incorporating into a tablet, capsule or other solid dosage form without first isolating or purifying said tannate salt complex of the active pharmaceutical ingredient.

2. The process according to claim 1 wherein the active pharmaceutical ingredient is selected from the group consisting of:
(1)carbinoxamine
(2)chlorpheniramine
(3)pyrilamine
(4)pheniramine
(5)phenindamine
(6)diphenhydramine
(7)bromodiphenydramine
(8)triplennamine
(9)brompheniramine
(10)loratadine
(11)desloratidine
(12)fexofenadine
(13)carbetapentane
(14)dextromethorphan
(15)phenylephrine
(16)pseudoephedrine
(17)ephedrine
(18)oxycodone
(19)morphine
(20)physostigmine
(21)cimetidine
(22)amantidine
(23)fluvoxamine
(24)sertraline
(25)chlorpromazine
(26)imipramine
(27)amitryptyline
(28)prochlorperazine
(29)cetirizine
(30)hydroxyzine
(31)promethazine

(32) acrivastine
(33) triprolidine
(34) meclizine
(35) dimenhydrinate
(36) dexchlorpheniramine
(37) doxylamine
(38) diphenylpyrilamine
(39) trimeprazine
(40) chlorcylizine
(41) triphennamine
(42) codeine
(43) cyproheptadine
(44) phenyltoloxamine
(45) clemastine
(46) famotidine
(47) hydrocodone
(48) methscopolamine
(49) ncostigmine
(50) gabapentin
(51) lithium compounds
(52) dopamine
(53) bromocriptine
(54) carbamazepine
(55) desipramine
(56) nortriptyline
(57) quinidine
(58) procainamide
(59) ranitidine
(60) quinine.

3. The process according to claim 1 wherein the active pharmaceutical ingredients are provided as the bitartrate, maleate, citrate, chloride, bromide, acetate or sulfate salt.

4. The process according to claim 1 wherein the tannic acid is provided as natural or synthetic.

5. The process of claim 1 wherein said anti-clumping agent is selected from a group consisting of magnesium aluminum silicate, xanthan gum and cellulose compounds.

6. The process according to claim 1 wherein the pharmaceutically acceptable liquid is selected from the group consisting of purified water, isopropyl alcohol, ethanol, glycerin, propylene glycol, mineral oil and mixtures thereof.

7. The process according to claim 6 wherein the pharmaceutically acceptable liquid is purified water.

8. The process according to claim 1 wherein the tannic acid is present as a dry powder and a powder blend is produced.

9. The process according to claim 1 wherein an excess by weight of tannic acid is provided at about three times the amount of active pharmaceutical ingredient.

10. The process according to claim 1 wherein a non-tannate salt of an active pharmaceutical ingredient is blended with the tannate salt complex.

11. The process according to claim 1 wherein the at least one active pharmaceutical ingredient is carbetapentane citrate, phenylephrine hydrochloride and chlorpheniramine maleate.

12. The process according to claim 1 wherein the at least one active pharmaceutical ingredient is pyrilamine maleate and phenylephrine hydrochloride.

13. The process according to claim 1 wherein the at least one active pharmaceutical ingredient is diphenhydramine hydrochloride.

14. The process according to claim 1, further comprising incorporating the tannate salt complex of the active ingredient into a therapeutic tablet, capsule or other solid dosage form.

15. The process according to claim 1 wherein the salt or free base of the active pharmaceutical ingredient is dissolved in a pharmaceutically acceptable liquid to form a solution at a maximum temperature and pH value that does not cause decomposition of the active pharmaceutical ingredient.

16. A process for preparing a tannate salt complex of at least one active pharmaceutical ingredient selected from a group consisting of an antihistamine, a decongestant, an antitussive and an anticholinergic comprising:

reacting a salt or free base of the at least one active pharmaceutical ingredient with an anti-clumping agent and tannic acid in a pharmaceutically acceptable liquid to form a reaction solution;

directly combining said reaction solution with a pharmaceutically acceptable excipient without isolation or purification to generate a therapeutic solid dosage form.

17. A therapeutic tannate composition for the treatment of symptoms associated with upper respiratory conditions in warm-blooded animals in need of such treatment, said composition comprising a therapeutically effective amount of (a) at least one active pharmaceutical ingredient selected from a group consisting of an antihistamine, a decongestant, an antitussive and an anticholinergic, tannic acid and an anti-clumping agent (b) tannic acid and (c) an anti-clumping agent where said composition has been prepared by combining the at least one active pharmaceutical ingredient, the tannic acid and the anti-clumping agent in the presence of a pharmaceutically acceptable liquid to form a tannate salt complex, and incorporating said tannate salt complex into a tablet, capsule or solid dosage form without first isolating or purifying said tannate salt complex of the at least one active pharmaceutical ingredient.

* * * * *

UNITED STATES PATENT AND TRADEMARK OFFICE
CERTIFICATE OF CORRECTION

| | |
|---|---|
| PATENT NO. | : 7,273,623 B2 |
| APPLICATION NO. | : 10/269027 |
| DATED | : September 25, 2007 |
| INVENTOR(S) | : Kiel et al. |

It is certified that error appears in the above-identified patent and that said Letters Patent is hereby corrected as shown below:

Col. 10, lines 38-41, please replace "from a group consisting of an antihistamine, decongestant, an antitusive and an anticholinergic, tannic acid and an" with -- from a group consisting of an antihistamine, a decongestant, an antitussive and an anticholinergic --

Signed and Sealed this

Twentieth Day of May, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,273,623 B2 |
| APPLICATION NO. | : 10/269027 |
| DATED | : September 25, 2007 |
| INVENTOR(S) | : Kiel et al. |

It is certified that error appears in the above-identified patent and that said Letters Patent is hereby corrected as shown below:

Col. 10, line 41, please remove the phrase "anti-clumping agent" (first occurrence)

Signed and Sealed this

Twelfth Day of May, 2009

JOHN DOLL
*Acting Director of the United States Patent and Trademark Office*